United States Patent
Lee et al.

(10) Patent No.: US 10,441,632 B2
(45) Date of Patent: Oct. 15, 2019

(54) ANTI-WRINKLE AND ANTI-AGING COSMETIC COMPOSITION COMPRISING GREEN FLUORESCENT PROTEIN-HUMAN EPIDERMAL GROWTH FACTOR FUSION PROTEIN AS EFFECTIVE COMPONENT

(71) Applicants: NEXGEN BIOTECHNOLOGIES, INC., Seoul (KR); Sun Kyo Lee, Gyeonggi-do (KR)

(72) Inventors: Sun Kyo Lee, Gyeonggi-do (KR); Seong Ran Lee, Gyeonggi-do (KR); Han Bong Ryu, Seoul (KR); Tae Hyun Kim, Gyeonggi-do (KR); Tae Won Choi, Seoul (KR); Hyeong Il Kwon, Seoul (KR)

(73) Assignees: NEXGEN BIOTECHNOLOGIES, INC., Seoul (KR); Sun Kyo Lee, Gyeonggi-Do (KR)

(*) Notice: Subject to any disclaimer, the term of this patent is extended or adjusted under 35 U.S.C. 154(b) by 0 days.

(21) Appl. No.: 16/071,009

(22) PCT Filed: Jan. 25, 2017

(86) PCT No.: PCT/KR2017/000909
§ 371 (c)(1),
(2) Date: Jul. 18, 2018

(87) PCT Pub. No.: WO2017/131448
PCT Pub. Date: Aug. 3, 2017

(65) Prior Publication Data
US 2019/0022184 A1 Jan. 24, 2019

(30) Foreign Application Priority Data
Jan. 29, 2016 (KR) ........................ 10-2016-0011663

(51) Int. Cl.
| A61K 38/18 | (2006.01) |
| A61K 8/64 | (2006.01) |
| A61Q 19/08 | (2006.01) |
| A61K 8/98 | (2006.01) |
| C07K 14/435 | (2006.01) |
| C07K 14/485 | (2006.01) |
| A61K 8/02 | (2006.01) |
| A61K 38/17 | (2006.01) |

(52) U.S. Cl.
CPC ............ *A61K 38/1808* (2013.01); *A61K 8/02* (2013.01); *A61K 8/64* (2013.01); *A61K 8/98* (2013.01); *A61K 8/987* (2013.01); *A61K 38/1767* (2013.01); *A61Q 19/08* (2013.01); *C07K 14/43595* (2013.01); *C07K 14/485* (2013.01); *C07K 14/43504* (2013.01); *C07K 2319/00* (2013.01); *C07K 2319/60* (2013.01)

(58) Field of Classification Search
None
See application file for complete search history.

(56) References Cited

U.S. PATENT DOCUMENTS 9,321,821 B2 * 4/2016 Lee ........................ C07K 14/50

FOREIGN PATENT DOCUMENTS

| EP | 1265990 B1 | 3/2006 |
| JP | 2015-74651 A | 4/2015 |
| KR | 10-1175803 B1 | 8/2012 |
| KR | 10-1238706 B1 | 3/2013 |
| KR | 10-2014-0091986 A | 7/2014 |
| KR | 10-2015-0060763 A | 6/2015 |
| WO | WO 01/34806 A2 | 5/2001 |
| WO | WO 2014/046481 A1 | 3/2014 |

OTHER PUBLICATIONS

Machine translation of KR20140091986 (published Jul. 23, 2014).*
International Search Report for PCT/KR2017/000909 dated Apr. 20, 2017.

* cited by examiner

*Primary Examiner* — Marianne P Allen
(74) *Attorney, Agent, or Firm* — The PL Law Group, PLLC (57) ABSTRACT

A method for treating wrinkle or aging on a skin of a subject includes applying to the skin a composition that includes a green fluorescent protein-human epidermal growth factor fusion protein as an effective component. Since the fusion protein has an excellent anti-oxidation activity and a high skin cell proliferation effect, it can be advantageously used as a raw material of functional cosmetics having excellent skin regeneration effect like improvement of skin wrinkles and skin whitening.

3 Claims, 3 Drawing Sheets
Specification includes a Sequence Listing.

SEQUENCE LISTING

<160> NUMBER OF SEQ ID NOS: 2

<210> SEQ ID NO 1
<211> LENGTH: 238
<212> TYPE: PRT
<213> ORGANISM: Aequorea victoria

<400> SEQUENCE: 1

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ala Tyr Gly Leu Gln Cys Phe Ala Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
```

```
                      165                 170                 175

Gln Leu Ala Asp His Tyr Gln Gln Asn Thr Pro Ile Gly Asp Gly Pro
                  180                 185                 190

Val Leu Leu Pro Asp Asn His Tyr Leu Ser Thr Gln Ser Ala Leu Ser
              195                 200                 205

Lys Asp Pro Asn Glu Lys Arg Asp His Met Val Leu Leu Glu Phe Val
          210                 215                 220

Thr Ala Ala Gly Ile Thr His Gly Met Asp Glu Leu Tyr Lys
225                 230                 235

<210> SEQ ID NO 2
<211> LENGTH: 291
<212> TYPE: PRT
<213> ORGANISM: Artificial Sequence
<220> FEATURE:
<223> OTHER INFORMATION: GFP-EGF

<400> SEQUENCE: 2

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Asn Ser
225                 230                 235                 240

Asp Ser Glu Cys Pro Leu Ser His Asp Gly Tyr Cys Leu His Asp Gly
                245                 250                 255

Val Cys Met Tyr Ile Glu Ala Leu Asp Lys Tyr Ala Cys Asn Cys Val
            260                 265                 270
```

```
Val Gly Tyr Ile Gly Glu Arg Cys Gln Tyr Arg Asp Leu Lys Trp Trp
        275                 280                 285
Glu Leu Arg
    290
```

ANTI-WRINKLE AND ANTI-AGING COSMETIC COMPOSITION COMPRISING GREEN FLUORESCENT PROTEIN-HUMAN EPIDERMAL GROWTH FACTOR FUSION PROTEIN AS EFFECTIVE COMPONENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/000909, filed Jan. 25, 2017, which claims priority to the benefit of Korean Patent Application No. 10-2016-0011663 filed in the Korean Intellectual Property Office on Jan. 29, 2016, the entire contents of which are incorporated herein by reference.

TECHNICAL FIELD

The present invention relates to an anti-wrinkle and anti-aging cosmetic composition comprising, as an effective component, a green fluorescent protein-human epidermal growth factor fusion protein having excellent skin regeneration effect and anti-oxidation activity.

BACKGROUND ART

Skin is composed of epidermis, dermis, and subcutaneous tissue. While providing protection against an attack by microbes that are introduced from an outside, skin plays a very important role for maintaining body moisture and body temperature. Epidermis plays a role of protecting skin, regulating body temperature, and maintaining body moisture, and it is composed of an extracellular matrix which is related with skin elasticity and skin flexibility. Dermis is directly related with skin aging.

Upon binding to a receptor for an epidermal growth factor present on a surface of a cell, the human epidermal growth factor (hEGF) induces a dimerization of a receptor for an epidermal growth factor. A dimeric receptor for an epidermal growth factor activates the tyrosine kinase present in the receptor to induce an intracellular signal transduction system. As a result of those processes, glycolysis and protein synthesis are promoted in a cell, eventually leading to cell growth.

The epidermal growth factor playing an important role in skin regeneration decreases according to a progress of aging, and a decrease in the epidermal growth factor causes a reduction in skin cell proliferation and transfer, and thus phenomena like skin aging, increased wrinkles, and reduced skin elasticity are exhibited accordingly.

Green fluorescent protein consisting of 238 amino acids is a protein with size of about 27 kDa in which a β barrel structure is formed by eleven β sheet structures and a loop structure is present both above and beneath the green fluorescent protein. Serine 65-tyrosine 66-glycine 67 are present inside the β barrel, and as a fluorophore is formed of those three amino acids, green fluorescence is generated.

The inventors of the present invention have studied to develop a new protein which has a skin regeneration activity of the human epidermal growth factor and is useful for protecting skin against active oxygen as a cause of aging. As a result, according to fusion of the green fluorescent protein originating from crystal jellyfish (*Aequorea victoria*) to human epidermal growth factor, they developed a fusion protein having not only excellent skin regeneration effect but also anti-oxidation activity.

Incidentally, in Korean Patent Registration No. 1175803, 'Cosmetic composition for skin cell regeneration and wrinkle improvement' comprising acetyl hexapeptide-3, copper peptide, palmitoyl pentapeptide, and epidermal growth factor is disclosed, and in Korean Patent Registration No. 1238706, 'Fermented camellia infused oil containing oils from *Acanthopanax Koreanum* as effective ingredient, preparation method thereof and anti-oxidation, anti-aging, anti-inflammatory, skin-whitening, anti-wrinkle, or anti-allergy cosmetic composition containing the same as active ingredient' is disclosed. However, there is no description relating to an anti-wrinkle and anti-aging cosmetic composition which comprises, as an effective component, the green fluorescent protein-human epidermal growth factor fusion protein of the present invention having excellent anti-oxidation activity.

SUMMARY

The present invention is devised under the circumstances described above, and the inventors of the present invention produces a novel green fluorescent protein-human epidermal growth factor fusion protein having excellent anti-oxidation activity according to fusion of a human epidermal growth factor protein, which is known to have an excellent cell regeneration effect, to a green fluorescent protein originating from jellyfish. Compared to the human epidermal growth factor protein alone, the fusion protein not only exhibits a high free radical scavenging activity but also has an excellent cell proliferation effect for skin fibroblasts. As a result of carrying out a skin test after preparing various cosmetic formulations, the wrinkle improving and skin whitening effect was confirmed from the testees, and the present invention is completed accordingly.

To solve the problems described above, the present invention provides an anti-wrinkle and anti-aging cosmetic composition which comprises a green fluorescent protein-human epidermal growth factor fusion protein as an effective component.

As the green fluorescent protein-human epidermal growth factor fusion protein of the present invention has an excellent anti-oxidation activity and high skin cell regeneration effect compared to the human epidermal growth factor protein alone, it can be advantageously used as a raw material of an anti-aging cosmetic composition having excellent skin regeneration effect like improvement of skin wrinkles and skin whitening.

DETAILED DESCRIPTION

To achieve the object of the present invention, the present invention provides an anti-wrinkle and anti-aging cosmetic composition comprising a green fluorescent protein-human epidermal growth factor fusion protein as an effective component.

The cosmetic composition of the present invention comprises, as an effective component, a fusion protein of the human epidermal growth factor protein having a skin regeneration effect and the green fluorescent protein having an excellent anti-oxidation activity, and thus it is a cosmetic composition having a function of improving wrinkles based on skin cell regeneration and also an anti-aging function based on anti-oxidation activity.

With regard to the cosmetic composition according to one embodiment of the present invention, the green fluorescent protein may originate from a jellyfish, and preferably from a crystal jellyfish (Aequorea victoria), but it is not limited thereto.

The scope of the green fluorescent protein originating from jellyfish according to the present invention includes a protein having an amino acid sequence represented by SEQ ID NO: 1, and also functional equivalents of the protein. The term "functional equivalent" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 1, and it indicates a protein exhibiting substantially the same activity as the protein represented by SEQ ID NO: 1. As described herein, the expression "substantially the same activity" means an anti-oxidation activity.

The scope of the green fluorescent protein-human epidermal growth factor fusion protein according to the present invention includes a protein having an amino acid sequence represented by SEQ ID NO: 2, and also functional equivalents of the protein. The term "functional equivalent" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 2, and it indicates a protein exhibiting substantially the same activity as the protein represented by SEQ ID NO: 2. As described herein, the expression "substantially the same activity" means a wrinkle improving effect based on skin regeneration while maintaining the anti-oxidation activity.

In the cosmetic composition according to one embodiment of the present invention, content of the fusion protein is preferably 0.000002 to 0.002% by weight relative to the total weight of the cosmetic composition.

In the cosmetic composition of the present invention, components that are typically used for a cosmetic composition can be included in addition to the effective components that are described above. Examples thereof include a lipid material, an organic solvent, a dissolution agent, a condensation agent, a gelling agent, a softening agent, an anti-oxidant, a suspension agent, a stabilizer, a foaming agent, an aroma, a surface active agent, water, an ionic or non-ionic emulsifier, a filler, a metal ion sequestering agent, a chelating agent, a preservative, vitamin, a blocking agent, a moisturizing agent, essential oil, a dye, a pigment, a hydrophilic or lipophilic activating agent, a common auxiliary agent such as lipid vesicle, and a carrier.

The composition of the present invention can be prepared in any formulation which is generally prepared in the pertinent art. For example, the composition may be formulated into a solution, a suspension, an emulsion, a paste, a gel, a crème, a lotion, a powder, an oil, a powder foundation, an emulsion foundation, a wax foundation, a spray, or the like, but not limited thereto.

More specifically, it can be prepared as a cosmetic formulation like a skin lotion, a skin softener, a skin toner, an astringent, a lotion, a milk lotion, a moisturizing lotion, a nutrition lotion, a massage crème, a nutrition crème, an eye crème, a moisturizing crème, a hand crème, an essence, a nutrition essence, a pack, a cleansing foam, a cleansing water, a cleansing lotion, a cleansing crème, a body lotion, a body cleanser, a soap, and a powder.

In a case in which the cosmetic composition of the present invention has a formulation type of paste, crème, or gel, it is possible to use animal oil, plant oil, wax, paraffin, starch, tragacanth, cellulose derivatives, polyethylene glycol, silicone, bentonite, silica, talc, or zinc oxide as a carrier component.

In a case in which the cosmetic composition of the present invention has a formulation type of powder or spray, it is possible to use lactose, talc, silica, aluminum hydroxide, calcium silicate, or polyamide powder as a carrier component. In particular, in a case in which the cosmetic composition is a spray, a propellant such as chlorofluorohydrocarbon, propane/butane, or dimethyl ether may be additionally included.

In a case in which the cosmetic composition of the present invention has a formulation type of solution or emulsion, a solvent, a dissolution agent, or an emulsifier is used as a carrier component, and examples thereof include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, and fatty acid ester of sorbitan.

In a case in which the cosmetic composition of the present invention has a formulation type of suspension, it is possible to use, as a carrier component, a liquid phase diluent such as water, ethanol, or propylene glycol, a suspension agent such as ethoxylated isostearyl alcohol, polyoxyethylene sorbitol ester, or polyoxyethylene sorbitan ester, microcrystalline cellulose, aluminum metahydroxide, bentonite, agar, or tragacanth.

Hereinbelow, the present invention is explained in greater detail in view of the Examples. However, it is evident that the following Examples are given only for exemplification of the present invention and by no means the present invention is limited to the following Examples.

Example 1. Induced Expression and Isolation of Green Fluorescent Protein-Human Epidermal Growth Factor Fusion Protein As a method for preparing a gene construct to produce the green fluorescent protein-human epidermal growth factor fusion protein and a method for producing the green fluorescent protein-human epidermal growth factor fusion protein by using the gene construct, E. coli ROSETTA2 (DE3) pLysS, which is transformed E. coli provided in Korean Patent Registration No. 1482187 (NEXGEN Biotechnologies, Inc.), was cultured, in case of batch culture, in 1 l LB or BSB medium till to have $OD_{600}$ value of 0.6 to 0.8, or cultured using a 20 l, fermenter till to have $OD_{600}$ value of 15 to 20 in case of continuous culture. Thereafter, by adding 1 to 5 mM IPTG or 2% lactose, expression of the cloned gene was induced. Culture was further continued for 4 to 5 hours after inducing the gene expression, and then the cells were collected by centrifuge. The obtained cells were thoroughly suspended in a buffer solution (phosphate buffered saline, NaCl 8 g, KCl 0.2 g, Na$_2$HPO$_4$ 1.44 g, KH$_2$PO$_4$ 0.24 g/t, pH 7.4). By disrupting the cells using an ultrasonic homogenizer, a solution containing the intracellular proteins was obtained. Thereafter, the protein-containing cell solution was subjected to a further procedure using Sepabeads Resin Brominated Styrenic Adsorbent (Sorbent Technologies, Inc., USA) to finally isolate and purify GFP-EGF.

Figure 1:
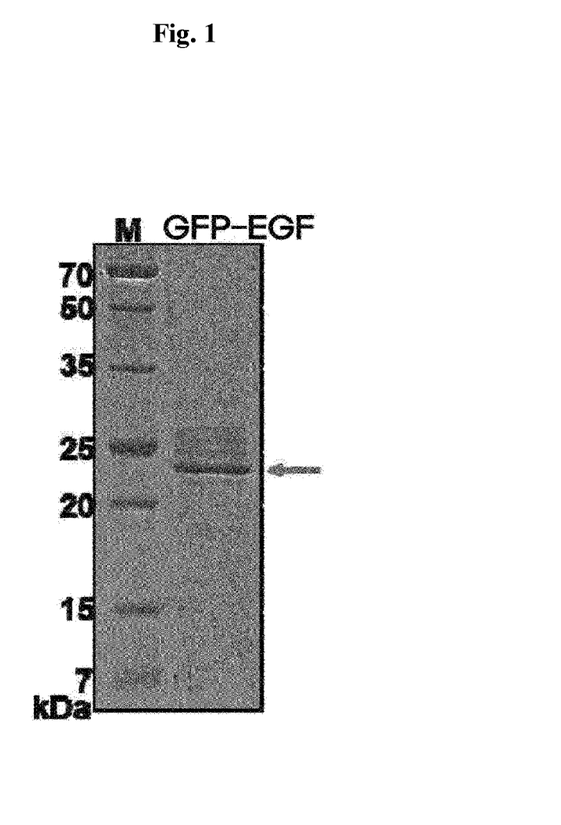
FIG. 1 shows the result that expression of the green fluorescent protein-human epidermal growth factor fusion protein is confirmed by SDS-polyacrylamide gel in which GFP-EGF indicates the green fluorescent protein-human epidermal growth factor fusion protein.

In order to determine the presence or absence of a fusion protein in the solution, 15% SDS-polyacrylamide gel electrophoresis was carried out. As a result, it was possible to confirm that the green fluorescent protein-human epidermal growth factor fusion protein is present in the sample (FIG. 1).

Example 2. Measurement of Anti-Oxidation Activity of Green Fluorescent Protein-Human Epidermal Growth Factor Fusion Protein In order to measure the anti-oxidation activity of green fluorescent protein-human epidermal growth factor fusion protein, DPPH (1,1-diphenyl-2-picryl hydrazyl) analysis, which is one of the methods to measure the free radical scavenging effect, was carried out.

Figure 2:
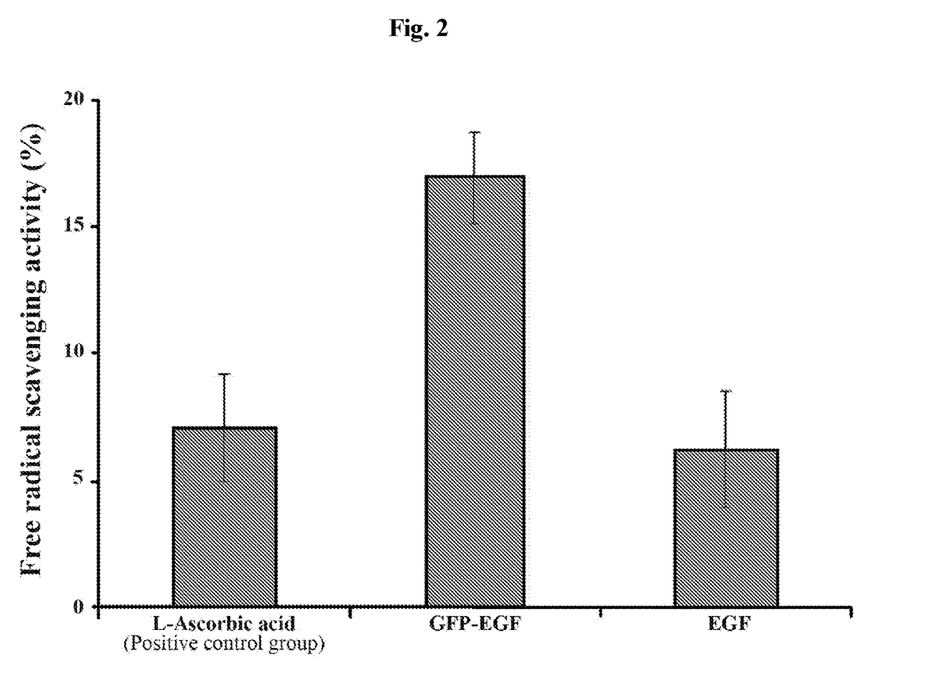
FIG. 2 shows the result of DPPH test to examine the anti-oxidation effect of the green fluorescent protein-human epidermal growth factor fusion protein.

For DPPH analysis, L-ascorbic acid was used as a control. As for the test method, each of L-ascorbic acid, the green fluorescent protein-human epidermal growth factor fusion protein, and human epidermal growth factor protein was prepared at 10 μM concentration while DPPH was prepared to have final concentration of 200 μM. After mixing each of the above proteins with DPPH at a ratio of 1:1, they were allowed to stand for 30 minutes at 37° C. Thereafter, absorbance at 520 nm was measured by using an ELISA reader. The free radical scavenging activity (%) was calculated based on the following formula 1, and the results are shown in FIG. 2.

Free radical scavenging activity (%)=100−((B/A)×100)   (Formula 1)

[A: Absorbance of control group not treated with sample
B: Absorbance of control group or test group treated with sample]

As a result, it was found that the green fluorescent protein-human epidermal growth factor fusion protein exhibited the free radical scavenging activity which is about 2.5 times higher than the ascorbic acid as a control group. Furthermore, even when compared to the human epidermal growth factor protein which has not been fused with the green fluorescent protein, it exhibited the free radical scavenging activity which is at least about 2.5 times higher (FIG. 2). Accordingly, it was possible to confirm that the fusion protein of the present invention can have a high anti-oxidation effect due to the green fluorescent protein, and this means that an anti-skin aging effect can be exhibited based on the excellent anti-oxidation effect of the fusion protein.

Example 3. Cell Proliferation Effect of Green Fluorescent Protein-Human Epidermal Growth Factor Fusion Protein A fraction from which the presence of the green fluorescent protein-human epidermal growth factor fusion protein finally isolated and purified in Example 1 has been confirmed was selected as a sample, and used for determination of the cell proliferation effect in HDFa cell (Human Dermal Fibroblasts adult).

Figure 3:
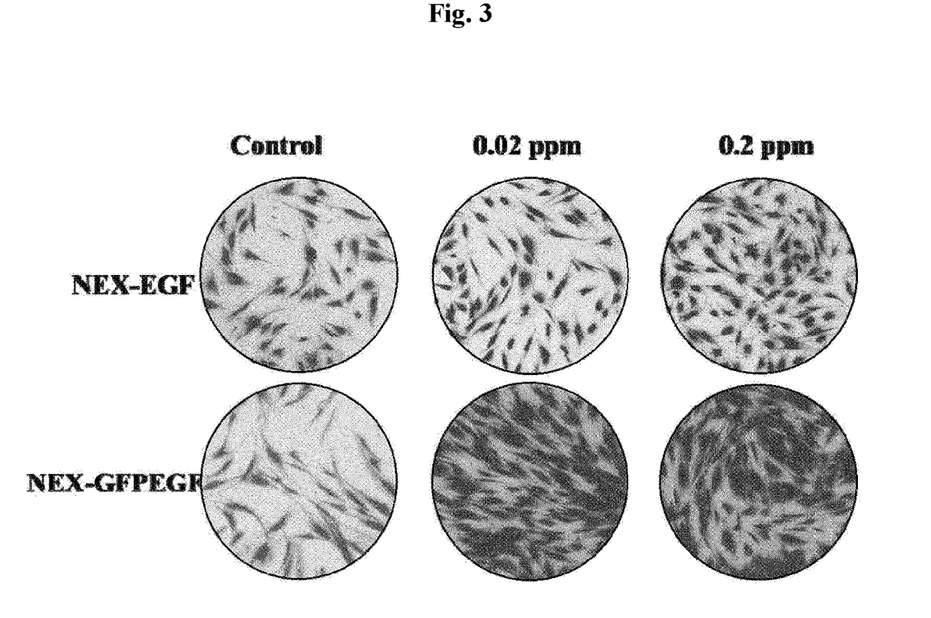
FIG. 3 is a photographic image from which the cell proliferation effect of the green fluorescent protein-human epidermal growth factor fusion protein in dermal fibroblasts is confirmed based on crystal violet staining.

To measure the cell proliferation activity of the green fluorescent protein-human epidermal growth factor fusion protein, cultured HDFa cells were further cultured for 3 days at 37° C. after treating them with the fusion protein or human epidermal growth factor protein not fused with green fluorescent protein at a concentration of 0, 0.02 ppm, or 0.2 ppm. Thereafter, presence or absence of cell proliferation was determined based on crystal violet staining method. As a result, it was possible to confirm the cell proliferation effect in HDFa cells in accordance with an increase in the treatment concentration of fusion protein. It was also confirmed that the cell proliferation effect of the fusion protein is more excellent than the cell proliferation obtained by a treatment with human epidermal growth factor protein alone (FIG. 3).

Based on the above results, it was confirmed that the green fluorescent protein-human epidermal growth factor fusion protein has not only an excellent anti-oxidation effect but also an anti-wrinkle effect.

Test Example 1. Sensory Skin Irritation Test Regarding Skin Regeneration Activity Like Wrinkle Improvement and Skin Whitening and Anti-Oxidation Effect Cosmetic compositions of Preparation examples 1, 2, 3, and 4, in which the green fluorescent protein-human epidermal growth factor fusion protein isolated and purified in Example 1 is contained as an effective component, and cosmetic compositions of Comparative example 1, 2, 3, and 4 were prepared and used for a sensory test.

Specifically, in order to determine an anti-wrinkle effect among the items relating to skin regeneration activity, total 30 people including men and women between the age of 30 and 59 (i.e., 10 people in 30 s, 10 people in 40 s, and 10 people in 50 s) were selected as a subject, and they were asked to apply the control group (Comparative example) to the area around the left eye or the test group (Preparation example) to the area around the right eye, once a day for 2 weeks continuously. The evaluation was carried out in terms of wrinkle smoothing around eye. Furthermore, with regard to the skin whitening as one of the activity-related items described above, the degree of a change in skin tone was also evaluated in the same manner as above. Furthermore, as for the anti-oxidation-related matter, the anti-aging effect was analyzed as an aging retardation effect, and relative comparison was made based on naked eye observation. As for the skin irritation, the sensory test was also carried out in the same manner as above regarding itchiness, stinging feeling, erythema of skin or the like. The evaluation was carried out based on the following evaluation criteria, i.e., 5-point scale including quite excellent (5 points), excellent (4 points), favorable (3 points), poor (2 points), and very poor (1 point). The results are shown in the following Tables 2, 4, 6 and 8.

Preparation Example 1 and Comparative Example 1

With or without adding the green fluorescent protein-human epidermal growth factor fusion protein (GFP-EGF) as an effective component, a skin composition was prepared with the components and content that are described in the following Table 1.

TABLE 1

Skin composition

| Component | Preparation example 1 (% by weight) | Comparative example 1 (% by weight) |
|---|---|---|
| GFP-EGF | 0.002 | — |
| Amino acid stock | 0.1 | 0.1 |
| Mixture of minerals | 0.0007 | 0.0007 |
| Purified water | Balance | Balance |

Result of the sensory test using Preparation example 1 and Comparative example 1 of above Table 1 is described in the following Table 2.

Preparation Example 2 and Comparative Example 2

With or without adding the green fluorescent protein-human epidermal growth factor fusion protein (GFP-EGF) as an effective component, an essence was prepared with the components and content that are described in the following Table 3.

TABLE 3

Essence composition

| Component | Preparation example 2 (% by weight) | Comparative example 2 (% by weight) |
|---|---|---|
| GFP-EGF | 0.002 | — |
| Amino acid stock | 0.05 | 0.05 |
| Mixture of minerals | 0.0007 | 0.0007 |
| Glycerol | 5 | 5 |
| 1,3-Butylene glycol | 10 | 10 |
| Carbopol 940 | 0.3 | 0.3 |
| Purified water | Balance | Balance |

Result of the sensory test using Preparation example 2 and Comparative example 2 of above Table 3 is described in the following Table 4.

TABLE 2

Result of Sensory Test of Preparation example 1 and Comparative example 1

| | | Skin regeneration | | | | Skin irritation |
|---|---|---|---|---|---|---|
| | | Wrinkle improvement | | Whitening | | |
| | Number | Preparation example | Comparative example | Preparation example | Preparation example | Preparation example |
| 30s | 1 | 4 | 3 | 4 | 3 | 4 |
| | 2 | 4 | 3 | 4 | 3 | 5 |
| | 3 | 4 | 3 | 3 | 3 | 4 |
| | 4 | 4 | 3 | 3 | 3 | 4 |
| | 5 | 3 | 2 | 3 | 2 | 3 |
| | 6 | 4 | 2 | 4 | 3 | 4 |
| | 7 | 4 | 3 | 4 | 3 | 4 |
| | 8 | 3 | 2 | 4 | 3 | 4 |
| | 9 | 4 | 2 | 4 | 3 | 5 |
| | 10 | 3 | 3 | 4 | 3 | 4 |
| 40s | 11 | 4 | 2 | 5 | 3 | 4 |
| | 12 | 4 | 2 | 5 | 2 | 4 |
| | 13 | 4 | 2 | 4 | 3 | 5 |
| | 14 | 4 | 3 | 5 | 2 | 5 |
| | 15 | 5 | 2 | 4 | 2 | 5 |
| | 16 | 4 | 3 | 4 | 2 | 4 |
| | 17 | 5 | 2 | 5 | 2 | 5 |
| | 18 | 4 | 3 | 4 | 3 | 5 |
| | 19 | 4 | 3 | 4 | 3 | 5 |
| | 20 | 4 | 3 | 5 | 2 | 4 |
| 50s | 21 | 5 | 2 | 4 | 3 | 5 |
| | 22 | 5 | 2 | 5 | 2 | 5 |
| | 23 | 5 | 2 | 5 | 2 | 5 |
| | 24 | 4 | 3 | 4 | 2 | 5 |
| | 25 | 4 | 2 | 4 | 2 | 4 |
| | 26 | 5 | 3 | 5 | 2 | 4 |
| | 27 | 5 | 2 | 5 | 3 | 5 |
| | 28 | 5 | 2 | 4 | 2 | 5 |
| | 29 | 4 | 2 | 5 | 3 | 5 |
| | 30 | 4 | 2 | 5 | 2 | 4 |
| | Mean value | 4.1 | 2.4 | 4.2 | 2.5 | 4.5 |

TABLE 4

Result of Sensory Test of Preparation example 2 and Comparative example 2

| | | Skin regeneration | | | Skin irritation |
|---|---|---|---|---|---|
| | | Wrinkle improvement | | Whitening | |
| | Number | Preparation example | Comparative example | Preparation example | Preparation example | Preparation example |
| 30s | 1 | 4 | 2 | 4 | 3 | 4 |
| | 2 | 4 | 2 | 4 | 3 | 5 |
| | 3 | 4 | 3 | 4 | 3 | 4 |
| | 4 | 4 | 2 | 3 | 3 | 4 |
| | 5 | 3 | 2 | 3 | 3 | 4 |
| | 6 | 4 | 2 | 4 | 3 | 4 |
| | 7 | 4 | 3 | 4 | 3 | 4 |
| | 8 | 3 | 2 | 4 | 3 | 4 |
| | 9 | 4 | 2 | 5 | 2 | 5 |
| | 10 | 4 | 3 | 4 | 3 | 4 |
| 40s | 11 | 5 | 2 | 5 | 2 | 5 |
| | 12 | 5 | 3 | 5 | 2 | 5 |
| | 13 | 4 | 2 | 5 | 2 | 5 |
| | 14 | 5 | 3 | 5 | 2 | 5 |
| | 15 | 5 | 2 | 4 | 2 | 5 |
| | 16 | 5 | 2 | 4 | 2 | 4 |
| | 17 | 5 | 2 | 5 | 2 | 5 |
| | 18 | 4 | 3 | 4 | 3 | 5 |
| | 19 | 5 | 2 | 4 | 2 | 5 |
| | 20 | 4 | 3 | 5 | 2 | 5 |
| 50s | 21 | 5 | 2 | 4 | 2 | 5 |
| | 22 | 5 | 2 | 5 | 2 | 5 |
| | 23 | 5 | 2 | 5 | 2 | 5 |
| | 24 | 4 | 2 | 4 | 2 | 5 |
| | 25 | 4 | 2 | 4 | 3 | 5 |
| | 26 | 5 | 3 | 5 | 2 | 4 |
| | 27 | 5 | 2 | 5 | 3 | 5 |
| | 28 | 5 | 2 | 4 | 2 | 5 |
| | 29 | 4 | 2 | 5 | 3 | 5 |
| | 30 | 5 | 1 | 5 | 2 | 4 |
| | Mean value | 4.4 | 2.2 | 4.3 | 2.4 | 4.6 |

Preparation Example 3 and Comparative Example 3

With or without adding the green fluorescent protein-human epidermal growth factor fusion protein (GFP-EGF) as an effective component, a lotion was prepared with the components and content that are described in the following Table 5.

TABLE 5

| | Lotion composition | |
|---|---|---|
| Component | Preparation example 3 (% by weight) | Comparative example 3 (% by weight) |
| GFP-EGF | 0.002 | — |
| Amino acid stock | 0.05 | 0.05 |
| Mixture of minerals | 0.0007 | 0.0007 |
| Glycerol | 3 | 3 |
| 1,3-Butylene glycol | 10 | 10 |
| Mineral oil | 5 | 5 |
| Cetyl alcohol | 2 | 2 |
| Xanthan gum | 0.5 | 0.5 |
| Purified water | Balance | Balance |

Result of the sensory test using Preparation example 3 and Comparative example 3 of above Table 5 is described in the following Table 6.

TABLE 6

Result of Sensory Test of Preparation example 3 and Comparative example 3

| | | Skin regeneration | | | Skin irritation |
|---|---|---|---|---|---|
| | | Wrinkle improvement | | Whitening | |
| | Number | Preparation example | Comparative example | Preparation example | Preparation example | Preparation example |
| 30s | 1 | 4 | 2 | 4 | 3 | 5 |
| | 2 | 4 | 2 | 4 | 2 | 5 |
| | 3 | 4 | 3 | 4 | 3 | 4 |
| | 4 | 3 | 2 | 3 | 3 | 4 |

TABLE 6-continued

Result of Sensory Test of Preparation example 3 and Comparative example 3

| | Number | Skin regeneration | | | | Skin irritation |
|---|---|---|---|---|---|---|
| | | Wrinkle improvement | | Whitening | | |
| | | Preparation example | Comparative example | Preparation example | Preparation example | Preparation example |
| | 5 | 3 | 2 | 4 | 3 | 4 |
| | 6 | 3 | 2 | 4 | 2 | 4 |
| | 7 | 4 | 3 | 4 | 3 | 5 |
| | 8 | 3 | 2 | 4 | 3 | 4 |
| | 9 | 4 | 2 | 5 | 2 | 5 |
| | 10 | 4 | 2 | 4 | 2 | 4 |
| 40s | 11 | 5 | 2 | 5 | 2 | 5 |
| | 12 | 5 | 3 | 5 | 2 | 5 |
| | 13 | 5 | 2 | 5 | 2 | 5 |
| | 14 | 5 | 2 | 5 | 2 | 5 |
| | 15 | 5 | 2 | 4 | 1 | 5 |
| | 16 | 5 | 1 | 4 | 2 | 4 |
| | 17 | 5 | 2 | 5 | 2 | 5 |
| | 18 | 4 | 3 | 4 | 3 | 5 |
| | 19 | 5 | 2 | 5 | 1 | 5 |
| | 20 | 5 | 1 | 5 | 2 | 5 |
| 50s | 21 | 5 | 2 | 4 | 2 | 5 |
| | 22 | 5 | 2 | 5 | 2 | 5 |
| | 23 | 5 | 2 | 5 | 2 | 5 |
| | 24 | 4 | 2 | 4 | 2 | 5 |
| | 25 | 4 | 2 | 4 | 1 | 5 |
| | 26 | 5 | 3 | 5 | 2 | 4 |
| | 27 | 5 | 2 | 5 | 3 | 5 |
| | 28 | 5 | 2 | 5 | 2 | 5 |
| | 29 | 5 | 2 | 5 | 3 | 5 |
| | 30 | 5 | 1 | 5 | 1 | 5 |
| | Mean value | 4.4 | 2.0 | 4.4 | 2.1 | 4.7 |

Preparation Example 4 and Comparative Example 4

With or without adding the green fluorescent protein-human epidermal growth factor fusion protein (GFP-EGF) as an effective component, a crème was prepared with the components and content that are described in the following Table 7.

TABLE 7

Creme composition

| Component | Preparation example 4 (% by weight) | Comparative example 4 (% by weight) |
|---|---|---|
| GFP-EGF | 0.002 | — |
| Amino acid stock | 0.05 | 0.05 |
| Mixture of minerals | 0.0007 | 0.0007 |
| Glycerol | 2 | 2 |
| Mineral oil | 10 | 10 |
| Olive emulsifying wax | 3 | 3 |
| Cetyl alcohol | 2 | 2 |
| Purified water | Balance | Balance |

Result of the sensory test using Preparation example 4 and Comparative example 4 of above Table 7 is described in the following Table 8.

TABLE 8

Result of Sensory Test of Preparation example 4 and Comparative example 4

| | Number | Skin regeneration | | | | Skin irritation |
|---|---|---|---|---|---|---|
| | | Wrinkle improvement | | Whitening | | |
| | | Preparation example | Comparative example | Preparation example | Preparation example | Preparation example |
| 30s | 1 | 4 | 3 | 3 | 2 | 5 |
| | 2 | 4 | 2 | 4 | 2 | 5 |
| | 3 | 4 | 3 | 4 | 2 | 4 |
| | 4 | 4 | 2 | 3 | 3 | 4 |
| | 5 | 3 | 3 | 3 | 3 | 4 |
| | 6 | 3 | 2 | 3 | 2 | 4 |
| | 7 | 4 | 3 | 4 | 3 | 5 |
| | 8 | 4 | 2 | 4 | 3 | 4 |

TABLE 8-continued

Result of Sensory Test of Preparation example 4 and Comparative example 4

|     | Number | Skin regeneration | | Whitening | | Skin irritation |
|     |        | Wrinkle improvement | | | | |
|     |        | Preparation example | Comparative example | Preparation example | Preparation example | Preparation example |
| --- | --- | --- | --- | --- | --- | --- |
| 40s | 9  | 4 | 2 | 4 | 2 | 5 |
|     | 10 | 4 | 3 | 4 | 2 | 4 |
|     | 11 | 5 | 3 | 5 | 2 | 5 |
|     | 12 | 5 | 3 | 5 | 2 | 5 |
|     | 13 | 5 | 2 | 4 | 2 | 5 |
|     | 14 | 5 | 2 | 5 | 2 | 5 |
|     | 15 | 5 | 2 | 5 | 3 | 5 |
|     | 16 | 5 | 2 | 4 | 2 | 4 |
|     | 17 | 5 | 2 | 4 | 2 | 5 |
|     | 18 | 4 | 3 | 4 | 3 | 5 |
|     | 19 | 5 | 2 | 5 | 2 | 5 |
|     | 20 | 5 | 2 | 4 | 2 | 5 |
| 50s | 21 | 5 | 2 | 4 | 2 | 5 |
|     | 22 | 5 | 2 | 5 | 2 | 5 |
|     | 23 | 5 | 2 | 5 | 2 | 5 |
|     | 24 | 4 | 2 | 5 | 2 | 5 |
|     | 25 | 4 | 2 | 4 | 2 | 5 |
|     | 26 | 5 | 3 | 5 | 2 | 4 |
|     | 27 | 5 | 2 | 5 | 3 | 5 |
|     | 28 | 5 | 2 | 5 | 2 | 5 |
|     | 29 | 5 | 2 | 5 | 3 | 5 |
|     | 30 | 5 | 2 | 5 | 2 | 5 |
|     | Mean value | 4.5 | 2.2 | 4.3 | 2.2 | 4.7 |

The invention claimed is:

1. A method for treating wrinkle or aging on a skin of a subject, the method comprising applying to the skin of the subject a composition comprising a green fluorescent protein-human epidermal growth factor fusion protein, wherein the green fluorescent protein-human epidermal growth factor fusion protein consists of the amino acid sequence of SEQ ID NO: 2.

2. The method of claim 1, wherein the green fluorescent protein-human epidermal growth factor fusion protein is included at 0.000002 to 0.002% by weight relative to the total weight of the composition.

3. The method of claim 1, wherein the composition has any one formulation selected from a group consisting of a skin lotion, a skin softener, a skin toner, an astringent, a lotion, a milk lotion, a moisturizing lotion, a nutrition lotion, a massage crème, a nutrition crème, an eye créme, a moisturizing créme, a hand créme, an essence, a nutrition essence, a pack, a cleansing foam, a cleansing water, a cleansing lotion, a cleansing créme, a body lotion, a body cleanser, a soap, and a powder.

* * * * *